US008025871B2

(12) United States Patent
Tokunaga

(10) Patent No.: US 8,025,871 B2
(45) Date of Patent: Sep. 27, 2011

(54) HAIR COSMETIC COMPOSITION

(75) Inventor: Shinichi Tokunaga, Sumida-ku (JP)

(73) Assignee: Kao Corporation, Tokyo (JP)

( * ) Notice: Subject to any disclaimer, the term of this patent is extended or adjusted under 35 U.S.C. 154(b) by 1144 days.

(21) Appl. No.: 11/454,934

(22) Filed: Jun. 19, 2006

(65) Prior Publication Data

US 2007/0071709 A1 Mar. 29, 2007

(30) Foreign Application Priority Data

Jun. 20, 2005 (JP) ................. 2005-179589

(51) Int. Cl.
*A61K 8/23* (2006.01)
*A61Q 5/12* (2006.01)

(52) U.S. Cl. .............. 424/70.5; 424/70.1; 424/70.6; 424/70.12; 424/70.27; 424/70.28; 424/70.31

(58) Field of Classification Search ............. 424/70.1
See application file for complete search history.

(56) References Cited

U.S. PATENT DOCUMENTS

| 5,114,706 | A | 5/1992 | Duvel |
| 6,358,502 | B1 | 3/2002 | Tanabe et al. |
| 7,585,989 | B2 * | 9/2009 | Kawashima et al. ........... 554/51 |
| 2002/0025302 | A1 * | 2/2002 | Morita et al. ............. 424/70.28 |
| 2002/0037266 | A1 | 3/2002 | Terazaki et al. |
| 2003/0147824 | A1 | 8/2003 | Terazaki et al. |
| 2003/0185783 | A1 | 10/2003 | Terazaki |

FOREIGN PATENT DOCUMENTS

| CN | 1086992 A | 5/1994 |
| CN | 1442129 A | 9/2003 |
| JP | 5-229919 | 9/1993 |
| JP | 8-92043 | 4/1996 |
| JP | 2000073085 A * | 3/2000 |
| JP | 2000-247841 | 9/2000 |
| JP | 2002-29938 | 1/2002 |
| JP | 2002-47141 | 2/2002 |
| JP | 2003-176212 | 6/2003 |
| JP | 2004-2261 | 1/2004 |
| JP | 2004-67534 | 3/2004 |
| JP | 2004-256551 | 9/2004 |
| WO | WO 94/06410 | 3/1994 |
| WO | WO 00/64412 | 11/2000 |

OTHER PUBLICATIONS

Iihara, T. et al. "Detergent Compsoition", JP 2000-073085, Jul. 3, 2000, machine translation.*
Terasaki, H. et al. "Hair Cosmetic", JP 2002-047141, Dec. 2, 2000, machine translation.*

* cited by examiner

*Primary Examiner* — Gina C Yu
(74) *Attorney, Agent, or Firm* — Oblon, Spivak, McClelland, Maier & Neustadt, L.L.P.

(57) ABSTRACT

Provided is a hair cosmetic composition containing Components (A) to (C), and having a pH (at 25° C.) of from 1 to 5.5 when diluted to 20 times its weight with water:

(A) a cationic surfactant, or a tertiary amine represented by the formula (1):

$$R^1-(A-R^4)_a-N\begin{matrix}R^2\\ \\R^3\end{matrix} \quad (1)$$

(wherein, at least one of $R^1$ to $R^3$ represents a $C_{8-23}$ aliphatic hydrocarbon and the remainder represents H, $C_{1-6}$ alkyl or hydroxyalkyl, or benzyl, $R^4$ represents a $C_{1-6}$ alkylene, A represents —CONH— or —NHCO—, and a stands for 0 or 1), (B) a $C_{8-30}$ aliphatic alcohol, and
(C) toluenesulfonic acid or salt thereof.

The hair cosmetic composition is excellent in the effect of restoring the flyaway or waved hair, which has appeared as a result of accumulation of damage due to hair coloring or the like, to its former state before damage and can give the hair good flexibility and smoothness during use of it.

18 Claims, No Drawings

HAIR COSMETIC COMPOSITION

FIELD OF THE INVENTION

The present invention relates to a hair cosmetic composition containing toluenesulfonates.

BACKGROUND OF THE INVENTION

Hair tends to be excessively dry because it is always exposed to sunlight and cannot avoid the influence of ultraviolet rays, heat and drying. Daily shampooing, brushing and blow drying also have an adverse influence. In recent years, it has been common to enjoy changing the appearance of hair freely such as changing hair color (coloring) and changing hair style (permanent waving) and coloring and permanent waving have been carried out with increased frequency. By the repetition of them, however, pores appear inside of the hair, which damages the dynamic physical properties of the hair, for example, deprives elasticity from the hair. In addition, an increase in the friction between the surfaces of individual hairs tends to cause entanglement of hair during shampooing or drying. Particularly at the hair end on which damage has accumulated, not only damage of dynamic physical properties of the hair and increase in surface friction occur but also waves-different from the original ones appear at the hair end, leading to "flyaway hair" or "jumping hair" meaning the state in which individual hairs go in various directions.

Various attempts have therefore been made to repair the damaged hair. With a view to repairing the hair having pores inside thereof and recovering the dynamic physical properties and optical physical properties of the hair, a hair cosmetic composition containing an organic acid, amino acid and cationic surfactant (JP-A-2000-247841) and a hair cosmetic composition having an organic acid, polypropylene glycol and cationic surfactant incorporated therein (JP-A-2002-29938 and JP-A-2002-47141) are, for example, proposed.

Although these hair cosmetic compositions can recover the dynamic and optical physical properties of the hair damaged by hair coloring or the like and give the hair flexibility and smoothness by reducing the friction on the surface of the hair, they cannot sufficiently remove the waves which have appeared as a result of accumulation of damages and restore the hair to its original state.

SUMMARY OF THE INVENTION

The present invention relates to a hair cosmetic composition containing the following components (A) to (C), and having a pH (at 25° C.) of from 1 to 5.5 when diluted to 20 times its weight with water:

(A) a cationic surfactant, or a tertiary amine represented by the formula (1):

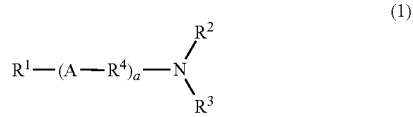

(wherein, at least one of $R^1$ to $R^3$ represents an aliphatic hydrocarbon group having from 8 to 23 carbon atoms and the remainder represents a hydrogen atom, an alkyl or hydroxyalkyl group having from 1 to 6 carbon atoms or a benzyl group, $R^4$ represents an alkylene group having from 1 to 6 carbon atoms, A represents —CONH— or —NHCO— and "a" stands for 0 or 1) or salt thereof:

(B) an aliphatic alcohol having from 8 to 30 carbon atoms, and (C) toluenesulfonic acid or a salt thereof.

DETAILED DESCRIPTION OF THE INVENTION

The present invention relates to a hair cosmetic composition excellent in the effect of restoring the hair, which has been flyaway or waved as a result of accumulation of damage due to hair coloring or the like, to its former state before damage and can give the hair good flexibility and smoothness during from wetting to drying, and after drying.

The present inventors have found that a hair cosmetic composition capable of satisfying the above-described requirements is available by using in combination at least one compound selected from cationic surfactants and specific tertiary amine compounds or salts thereof, a higher alcohol, and toluenesulfonic acid or a salt thereof.

As the cationic surfactant (A), quaternary ammonium salts or ether type quaternary ammonium salts can be used. Examples of the quaternary ammonium salts include those represented by the following formula (2):

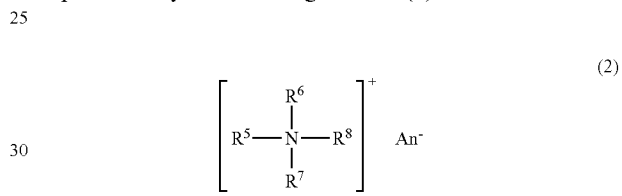

(wherein, $R^5$ and $R^6$ each represents a hydrogen atom, an alkyl group having form 1 to 28 carbon atoms or a benzyl group, with the proviso that they do not simultaneously represent a hydrogen atom or a benzyl group and at least one of them represents an alkyl group having 8 or more carbon atoms, $R^7$ and $R^8$ each represents an alkyl or hydroxyalkyl group having from 1 to 5 carbon atoms or a polyoxyethylene group whose added molar number is 10 or greater in total, and An⁻ represents an anion).

When $R^5$ or $R^6$ is an alkyl group, it has preferably from 16 to 24 carbon atoms, more preferably 22 carbon atoms. It is preferably a linear alkyl group. Examples of the An⁻ include halide ions such as chloride ion and bromide ion, and organic ions such as ethyl sulfate ion and methyl carbonate ion. Of them, halide ions are preferred, with chloride ion being preferred.

As the quaternary ammonium salt, mono(long chain) quaternary ammonium salts are preferred. Specific examples include behenyltrimethylammonium chloride, stearyltrimethylammonium chloride, cetyltrimethylammonium chloride and arachyltrimethylammonium chloride. Of these, behenyltrimethylammonium chloride and stearyltrimethylammonium chloride are preferred.

Examples of the ether type quaternary ammonium salt include compounds represented by the formula (3):

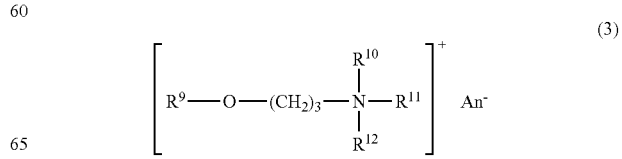

(wherein, $R^9$ represents a linear or branched alkyl or alkenyl group having from 6 to 24 carbon atoms, $R^{10}$ to $R^{12}$ each represents an alkyl group having from 1 to 6 carbon atoms, benzyl group or —$(BO)_nH$ (B representing an alkylene group having from 2 to 4 carbon atoms, n means an average number of moles added and it is from 1 to 6, and n pieces of B may be the same or different and may be arranged in any order), and $An^-$ represents an anion).

In formula (3), $R^9$ has preferably from 12 to 22 carbon atoms, more preferably from 16 to 18 carbon atoms. It is preferably a linear alkyl group. $R^{10}$ to $R^{12}$ are each preferably an alkyl group having from 1 to 6 carbon atoms or —$(CH_2CH_2O)_nH$ (in which n stands for 1 to 3, with 1 being more preferred), more preferably a methyl or ethyl group, still more preferably a methyl group. Of $R^{10}$ to $R^{12}$, $R^{11}$ is preferably a methyl or ethyl group, more preferably a methyl group. As $An^-$, those described above are preferred.

Examples of the ether type quaternary ammonium salt include stearoxypropyltrimethylammonium chloride.

As the tertiary amine compound, preferred are alkylamine compounds (1a), that is, compounds of the formula (1) in which a stands for 0, and amidoamine compounds (1b), that is, compounds of the formula (1) in which A represents —CONH— and a stands for 1.

(1a)

(wherein, at least one of $R^{13}$ to $R^{15}$ represents an aliphatic hydrocarbon group having from 8 to 23 carbon atoms and the remainder represents a hydrogen atom, an alkyl or hydroxyalkyl group having from 1 to 4 carbon atoms or a benzyl group, with the proviso that at least two of them do not simultaneously represent a hydrogen atom).

Specific examples of the alkylamine compound (1a) include dimethyldecylamine, dimethyllaurylamine, dimethylmyristylamine, dimethylpalmitylamine, dimethylstearylamine, dimethyloctylamine, dimethylbehenylamine, dilaurylmonomethylamine and trioctylamine.

Of these alkylamine compounds, those having, as one of $R^{13}$ to $R^{15}$, an aliphatic hydrocarbon group having from 8 to 23 carbon atoms and, as the other two, an alkyl or hydroxyalkyl group having from 1 to 4 carbon atoms are preferred. Specific preferred examples include dimethylpalmitylamine and dimethylstearylamine.

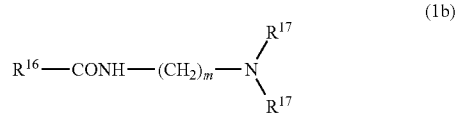

(1b)

(wherein, $R^6$ represents an aliphatic hydrocarbon group having from 11 to 23 carbon atoms, $R^{17}$s may be the same or different and each represents a hydrogen atom or an alkyl group having from 1 to 4 carbon atoms, and m stands for an integer of from 2 to 4).

Examples of the $R^{16}CO$ in the formula (1b) include lauroyl, myristoyl, palmitoyl, stearoyl, oleoyl and behenoyl groups. Examples of $R^{17}$ include methyl, ethyl and propyl, with methyl and ethyl are preferred. As m, 2 or 3 is preferred.

Specific examples of the amidoamine compound (1b) include stearic acid dimethylaminoethylamide, stearic acid dimethylaminopropylamide, stearic acid diethylaminoethylamide, stearic acid diethylaminopropylamide, stearic acid dipropylaminoethylamide, stearic acid dipropylaminopropylamide, palmitic acid dimethylaminoethylamide, palmitic acid dimethylaminopropylamide, myristic acid dimethylaminoethylamide, myristic acid dimethylaminopropylamide, behenic acid dimethylaminoethylamide and behenic acid dimethylaminopropylamide. From the viewpoints of performance, stability and easy availability, stearic acid diethylaminoethylamide, stearic acid dimethylaminopropylamide and behenic acid dimethylaminopropylamide are preferred.

The tertiary amine compound (A) is preferably neutralized with an acid. It is preferred to use, as the acid, at least one water soluble organic acid. Examples of the water soluble organic acid include alkylsulfuric acids, alkylphosphoric acids, monocarboxylic acids, dicarboxylic acids, hydroxycarboxylic acids, polycarboxylic acids and acidic aminoacids. Of these, carboxylic acids and acidic amino acids are preferred. As the carboxylic acids, dicarboxylic acids and hydroxycarboxylic acids are preferred. Specific examples of the dicarboxylic acids include malonic acid, succinic acid, glutaric acid, adipic acid, maleic acid, fumaric acid and phthalic acid, of which malonic acid, succinic acid and maleic acid are preferred. Examples of the hydroxycarboxylic acids include glycolic acid, lactic acid, hydroxyacrylic acid, oxybutyric acid (more preferably, α-oxybutyric acid), glyceric acid, malic acid, tartaric acid and citric acid. Of these, α-hydroxycarboxylic acid is preferred, with glycolic acid, lactic acid and malic acid being more preferred. Examples of the acidic amino acids include L-glutamic acid and L-aspartic acid, of which L-glutamic acid is preferred. The above-described organic acid is added preferably in an amount of from 0.1 to 10 times the mole, more preferably from 0.3 to 3 times the mole of the tertiary amine from the viewpoints of reduction in amine odor and heightening of the conditioning effects such as flexibility and smoothness.

As Component (A), the cationic surfactants and tertiary amine compounds or salts thereof may be used either singly or in combination of two or more of them. Component (A) is incorporated preferably in an amount of from 0.01 to 20 wt. %, more preferably from 0.1 to 10 wt. %, still more preferably from 0.5 to 5 wt. % in the hair cosmetic composition of the present invention from the viewpoint of good feeling upon use.

The aliphatic alcohol (B) having from 8 to 30 carbon atoms preferably has an alkyl group having from 12 to 28 carbon atoms, more preferably from 16 to 24 carbon atoms, still more preferably 22 carbon atoms. The alkyl group is preferably a linear alkyl group. Specific examples of the aliphatic alcohol include cetyl alcohol, stearyl alcohol, aralkyl alcohol and behenyl alcohol, of which stearyl alcohol and behenyl alcohol are preferred.

As Component (B), two or more aliphatic alcohols may be used in combination. Their content in the hair cosmetic composition of the present invention is preferably from 0.1 to 20.0 wt. %, more preferably from 0.5 to 10.0 wt. % from the standpoint of feeling upon use. The molar ratio of the cationic surfactant or tertiary amine or salt thereof as Component (A) to the aliphatic alcohol as Component (B) [Component (A)/Component (B)] is preferably from 0.8/2 to 0.8/15 from the standpoint of improvement in the stability of the hair cosmetic composition.

Examples of toluenesulfonic acid as Component (C) include o-toluenesulfonic acid and p-toluenesulfonic acid, while those of their salt include sodium salt, potassium salt and ammonium salt. The content of Component (C) in the hair cosmetic composition of the present invention is preferably from 0.01 to 5 wt. %, more preferably from 0.05 to 2 wt. %, still more preferably from 0.1 to 1 wt. % from the standpoint of a function of restoring the flyaway or waved hair, which has been caused by the accumulation of damage due to hair coloring or the like, to its former straight hair. It should be noted that the toluenesulfonic acid is preferably added not as a counterion of the cationic surfactant (A) or a neutralizing salt of the tertiary amine (A) but added separately from the viewpoint of exhibition of the above-described function. When the tertiary amine is used as Component (A), the total amount of toluenesulfonic acid as the neutralizing acid of the tertiary amine and Component (C) is preferably 1.0 molar equivalent or greater relative to Component (A) from the viewpoint of promoting the function of Component (C).

The hair cosmetic composition is adjusted to from pH 1 to 5.5 (at 25° C.) when diluted to 20 times its weight with water from the viewpoint of restoring the hair, which has been flyaway or waved as a result of accumulation of damage due to hair coloring or the like, to its former state. The pH is adjusted more preferably to from 2 to 5.5, still more preferably to from 2.5 to 5, still more preferably to from 3 to 4.5.

The hair cosmetic composition of the present invention preferably contains an organic solvent as Component (D) further in order to improve the function of restoring the hair, which has been flyaway or waved as a result of accumulation of damage due to hair coloring or the like, to its former straight hair state before damage. As the organic solvent, those described below can be used.

(d1) Compounds represented by the formula (4):

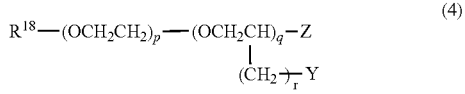
(4)

(wherein, $R^{18}$ represents a hydrogen atom, an alkyl group having from 1 to 6 carbon atoms or a group $R^{19}$-Ph-$R^{20}$— (in which $R^{19}$ represents a hydrogen atom, a methyl group or a methoxy group, $R^{20}$ represents a bond or a saturated or unsaturated divalent hydrocarbon group having from 1 to 3 carbon atoms, and Ph represents a paraphenylene group), Y and Z each represents a hydrogen atom or a hydroxyl group, p, q and r each stands for an integer of from 0 to 5, with the proviso that when p=q=0, Z represents a hydroxyl group and $R^{18}$ represents neither a hydrogen atom nor a group $R^{19}$-Ph-).

(d2) N-Alkylpyrrolidones having a $C_{1-18}$ alkyl group bonded to a nitrogen atom.

(d3) Alkylene carbonates having from 2 to 4 carbon atoms.

(d4) Propylene glycols having a molecular weight of from 200 to 5000.

(d5) Lactones or cyclic ketones represented by the following formula (5), (6) or (7):

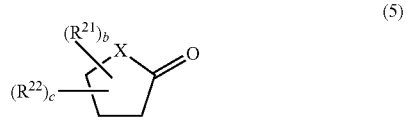
(5)

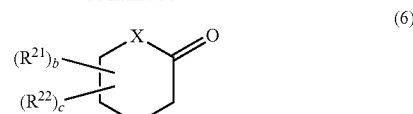
(6)

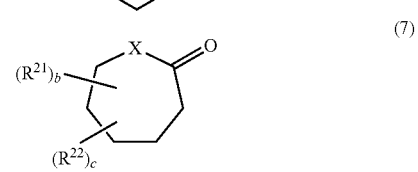
(7)

(wherein, X represents a methylene group or an oxygen atom, $R^{21}$ and $R^{22}$ each independently represents a substituent selected from linear, branched or cyclic $C_{1-10}$ alkyl groups which may be substituted with a sulfonic acid group, phosphoric acid group or carboxyl group, a hydroxyl group, a sulfonic acid group, a phosphoric acid group, a carboxyl group and a phenyl group, and b and c each stands for 0 or 1).

When p=q=0 and Z represents a hydroxyl group, examples of (d1) include monohydric alcohols such as ethanol, 1-propanol, 2-propanol, butanol and isobutanol, polyhydric alcohols such as ethylene glycol, propylene glycol, dipropylene glycol, 1,3-butanediol and glycerin, and aromatic alcohols having a group $R^{19}$-Ph-$R^{20}$— such as benzyl alcohol, cinnamyl alcohol, phenethyl alcohol, p-anisyl alcohol, p-methylbenzyl alcohol, phenoxyethanol and 2-benzyloxyethanol. Additional examples include methyl carbitol, ethyl carbitol, propyl carbitol, butyl carbitol, triethylene glycol monomethyl ether and triethylene glycol monobutyl ether.

Examples of (d2) include N-methylpyrrolidone, N-octylpyrrolidone and N-laurylpyrrolidone.

Examples of (d3) include ethylene carbonate and propylene carbonate.

The polypropylene glycol as (d4) preferably has a molecular weight of from 200 to 1000.

In (d5), $R^{21}$ and $R^{22}$ of the formula (5), (6) or (7) are each preferably a linear, branched or cyclic alkyl group, hydroxyl group, sulfonic acid group, phosphoric acid group, carboxyl group, phenyl group, sulfoalkyl group, alkyl phosphate group or carboxyalkyl group. A $C_{1-6}$ linear or branched alkyl group such as methyl, ethyl, propyl, isopropyl or butyl substituted at the γ-position in the case of γ-lactone and at the δ-position (that is, methylene adjacent to the hetero oxygen atom) in the case of δ-lactone is preferred. For enhancing the water solubility of Compounds (5) to (7), use of an acidic group such as sulfonic acid group, phosphoric acid group or carboxyl group or an alkyl group substituted therewith as $R^{21}$ or $R^{22}$ is preferred. As (d5), examples of the lactone include γ-butyrolactone, γ-caprolactone, γ-valerolactone, δ-valerolactone, δ-caprolactone, and δ-heptanolactone. From the viewpoint of stability of lactone, γ-lactone, of which γ-butyrolactone and γ-caprolactone are preferred. Examples of the cyclic ketone as d5 include cyclopentanone, cyclohexanone, cycloheptanone and 4-methylcycloheptanone.

Of these organic solvents, aromatic alcohols and polyhydric alcohols in (d1), alkylene carbonates in (d3) and polypropylene glycol in (d4) are preferred. Use of at least one aromatic organic solvent is more preferred in order to restore the hair, which has been flyway or waved as a result of accumulation of damage caused due to hair coloring or the like, to its former state. Two or more of these organic solvents may be used in combination.

The content of the organic solvent in the hair cosmetic composition of the present invention is preferably from 0.01 to 20 wt. %, more preferably from 0.1 to 15 wt. %, still more preferably from 0.5 to 10 wt. % in consideration of the above-described effects. With regard to a ratio of the organic solvent to water contained in the hair cosmetic composition, the organic solvent exists relative to water at a weight ratio less than 20:80 (organic solvent:water) in consideration of the performance of the composition capable of giving the hair good flexibility and smoothness during from wetting to drying and even after drying.

To the hair cosmetic composition of the present invention, a silicone compound can be added further for improving the manageability of the hair after drying. For example, silicones described below can be employed.

(1) Highly Polymerized Dimethylpolysiloxanes

Examples include "BY11-026" and "BY22-19" (each, product of Dow Corning Toray Silicone), and "FZ-3125" (product of Nippon Unicar). The highly polymerized dimethylpolysiloxane dissolved or dispersed in a liquid oil (for example, the below-described (ii) dimethylpolysiloxane oil, (iii) liquid silicone oil such as cyclic silicone or liquid hydrocarbon oil such as isoparaffin) can also be used.

(ii) Dimethylpolysiloxane oil represented by the formula (8):

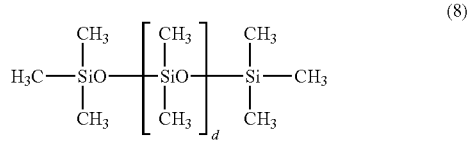

(wherein, d stands for an integer of from 0 to 650).

Specific examples include commercially available products such as "SH200C Fluid 1 cs, 50 cs, 200 cs, 1000 cs and 5000 cs" (each, product of Dow Corning Toray Silicone).

(iii) Cyclic silicone represented by the formula (9):

(wherein, e stands for an integer of from 3 to 7).

Specific examples include dodecamethylcyclohexasiloxane, octamethylcyclotetrasiloxane and decamethylcyclopentasiloxane. Examples of the commercially available product include "SH244" and "SH245" (each, product of Dow Corning Toray Silicone).

(iv) Amino-modified silicones represented by the formula (10):

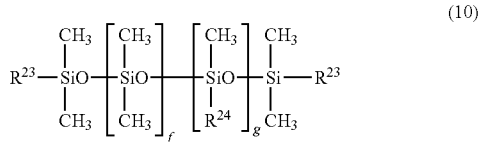

(wherein, $R^{23}$ represent a similar group to that of $R^{24}$ or a methyl or hydroxyl group, $R^{24}$ represents a reactive functional group represented by $—R^{25}—W$ (in which $R^{25}$ represents a divalent hydrocarbon group having from 3 to 6 carbon atoms and W represents a group containing a primary, secondary or tertiary amino group or an ammonium-containing group), and f and g each stands for a positive integer and f+g varies depending on the molecular weight. Preferable average molecular weight is from 3000 to 100000).

Examples include "SS-3551", "SF8452C", "DC929" and "DC8500" (each, product of Down Corning Toray Silicone) and "KT 1989" (product of GE Toshiba). When the amino-modified silicone is used in the form of a water-based emulsion, the amount of the amino-modified silicone contained in the water-based emulsion is preferably from 20 to 60 wt. %, more preferably from 30 to 50 wt. %. Preferred examples of the water-based emulsion of an amino-modified silicone include "SM8704C" (product of Dow Corning Toray Silicone).

(v) Other Silicones

Examples of the silicone other than those described above include polyether modified silicones, methylphenylpolysiloxane, fatty acid modified silicones, alcohol modified silicones, alkoxy modified silicones, epoxy modified silicones, fluorine modified silicones and alkyl modified silicones.

When the silicone compound is incorporated in the hair cosmetic composition of the present invention, its content therein is preferably from 0.1 to 15 wt. %, more preferably from 0.5 to 10 wt. %, still more preferably from 1.0 to 5 wt. % from the viewpoints of the manageability and retention of the styled hair.

The hair cosmetic composition of the present invention can further contain an oily component other than Component (B) and the above-described silicone for the purpose of improving the touch given to the hair and smooth combing property. Examples of the oily component include higher fatty acids such as capric acid, lauric acid, myristic acid, palmitic acid, stearic acid, behenic acid, oleic acid, coconut fatty acid, isostearic acid and isopalmitic acid; and hydrocarbon oils such as liquid paraffin, liquid isoparaffin, vaseline, squalene and squalane. Examples further include natural oils such as camellia oil, Macadamia nut oil, corn oil, olive oil, avocado oil, castor oil, safflower oil, jojoba oil, sunflower oil, rapeseed oil, sesame oil, soybean oil and meadow foam oil; and ester oils such as isopropyl myristate, isopropyl palmitate, myristyl myristate, octyl palmitate, stearyl stearate, isocetyl stearate, isononyl isononanoate, isotridecyl isononanoate, stearic acid hydrogenated castor oil, hydroxystearic acid hydrogenated castor oil, glyceryl tri-2-ethylhexanoate, pentaerythritol tetra-2-ethylhexanoate, neopentyl glycol dicaprate, diglyceryl diisostearate and esters with a mixed fatty acid such as dipentaerythritol and hydroxystearic acid/stearic acid/rosic acid. Oils or fats, for example, ceramides such as sphingoshines, e.g., dihydrosphingosine and phytosphingosine and N-acylated sphingosines, N-acylated phytosphingosines and N-acylated dihydrosphingosines available by the extraction of a synthetic or natural product can also be employed. Specific examples of them include Ceramide 1, Ceramide 2, Ceramide 3, Ceramide 1A, Ceramide 6II and hydroxycaproylphytosphingosine. Synthetic pseudo ceramides as described in JP-A-11-209248 and JP-A-01-042934 can also be used.

The hair cosmetic composition of the present invention may further contain, according to the using purpose, components ordinarily employed for hair cosmetic compositions. Examples include polymer compounds such as cationic cellulose, hydroxylated cellulose and highly polymerized polyethylene oxide, nonionic surfactants such as polyoxyethylene alkyl ethers, polyoxyethylene sorbitan fatty acid esters, glycerin fatty acid esters, polyglycerin fatty acid esters, polyoxyethylene hydrogenated castor oils, sucrose fatty acid esters, polyglycerin alkyl ethers, fatty acid alkanolamides, and alkyl glycosides, inorganic acids such as phosphoric acid, anti-dandruffs such as zinc pyrithione and benzalkonium chloride; vitamin preparations; bactericides; anti-inflammatory agents; antiseptics; chelating agents; humectants such as panthenol; colorants such as dyes and pigments; extracts such as extract of Eucalyptus in a polar solvent, protein available from a pearl or a shell having a pear layer or hydrolysate of the protein, protein available from silk or hydrolysate of the protein, protein-containing extract available from seeds of legume plants, Panax ginseng extract, rice bran extract, fucoid extract, camellia extract, aloe extract, Alpinia Leaf extract and chlorella extract; pearl powder such as mica titanium; perfumes; coloring matters; ultraviolet absorbers; antioxidants; and other components described in ENCYCLOPEDIA OF SHAMPOO INGREDIENTS (MICELLE PRESS).

The hair cosmetic composition of the present invention is prepared by dissolving Components (A) to (C) and other optional components in water, if necessary, in a solvent. It is provided, for example, as hair rinse, hair conditioner, and hair treatment.

EXAMPLES

In the following description, "pH" is a value as measured at 25° C. when a hair cosmetic composition is diluted to 20 times its weight with water.

Examples 1 to 7 and Comparative Examples 1 to 4

The hair cosmetic compositions (hair conditioners) shown in Table 1 were prepared in a manner known per se in the art and they were organoleptically evaluated in accordance with the following procedure.

(Smoothness During Application•Rinsing)

A hair bundle of 20 cm in length, 5.5 cm in width and 10.0 g in weight was prepared using hair damaged by repeating eight times of bleaching and 720 times of shampooing and drying. The resulting hair bundle was washed well with 1.0 g of a plain shampoo (prepared from sodium polyoxyethylene (2.5) lauryl ether sulfate and diethanolamide). After water was drained off roughly, 1.0 g of each of the hair conditioners was applied. During application, the smoothness was evaluated. The hair bundle was then rinsed with 6 L/min running water of 40° C. for 30 seconds and the smoothness during rinsing was also evaluated. The evaluation was made a panel of five persons. Their total score is indicated in the below-described table.

Evaluation Criteria:
  4: Very smooth
  3: Smooth
  2: Not so smooth
  1: Not smooth (Effect of Restoring the Flyaway or Waved Hair End to its Former Straight State)

A hair bundle of 20 cm in length, 5.5 cm in width and 10.0 g in weight, which had been prepared using the hair damaged by repeating eight times of bleaching and 720 times of shampooing and drying, was washed well with 1.0 g of the plain shampoo. After water was drained off roughly, 1.0 g of each of the hair conditioners was applied. The hair bundle was then rinsed with 6 L/min running water of 40° C. for 30 seconds. After towel-drying, the hair bundle was dried sufficiently for 2 to 3 minutes by hot air from a hair drier. The above-described operation was repeated twenty times in total. By using the hair bundle which had finished 20-times repetition, the removal degree of the wave from the hair end was visually evaluated. Evaluation was made by a panel of five persons. Their total score is indicated in the below-described table.

Evaluation Criteria
  4: Waves have disappeared.
  3: Some waves have disappeared.
  2: Many waves have remained.
  1: Waves have not disappeared.

TABLE 1

| | Composition of conditioner (wt. %) | Examples | | | | | | | Comparative Examples | | | |
|---|---|---|---|---|---|---|---|---|---|---|---|---|
| | | 1 | 2 | 3 | 4 | 5 | 6 | 7 | 1 | 2 | 3 | 4 |
| (A) | Stearyltrimethylammonium chloride | 1.5 | | | | | | | | | | |
| | Behenyltrimethylammonium chloride | | 1.5 | | | | 0.75 | 1.5 | | 1.5 | 1.5 | 1.5 |
| | Dimethylstearylamine | | | 1.5 | | | | | | | | |
| | Stearamidopropyl dimethylamine | | | | 1.5 | | 0.75 | | | | | |
| | Stearoxypropyltrimonium chloride | | | | | 1.5 | | | | | | |
| (B) | Stearyl alcohol | 3 | 2 | 3 | 3 | 2 | 2 | 2 | 3 | | 2 | 2 |
| | Behenyl alcohol | 3 | 3 | 3 | 3 | 3 | 3 | 3 | 3 | | 3 | 3 |
| (C) | p-Toluenesulfonic acid | 0.1 | 0.1 | 0.1 | 0.1 | 0.1 | 0.1 | 0.5 | 0.1 | 0.1 | | 0.1 |
| (D) | 2-Benzyloxyethanol | | | | | | | 0.5 | | | | |
| | Dipropylene glycol | | | | | | | 1 | | | | |
| Other compo- nents | Lactic acid (90 wt. % aq. soln.) | 0.3 | 0.3 | 0.6 | 0.6 | 0.6 | 0.2 | 0.3 | 0.3 | 0.3 | 0.3 | 0.2 |
| | Malic acid (50 wt. % aq. soln.) | | | | | | 0.2 | | | | | |
| | Hydroxyethyl cellulose | 0.3 | 0.3 | 0.3 | 0.3 | 0.3 | 0.3 | 0.3 | 0.3 | 0.3 | 0.3 | 0.3 |
| | Deionized water | Balance | Balance | Balance | Balance | Balance | Balance | Balance | Balance | Balance | Balance | Balance |
| | pH Regulator | q.s. | q.s. | q.s. | q.s. | q.s. | q.s. | q.s. | q.s. | q.s. | q.s. | q.s. |
| | pH | 3.5 | 3.5 | 4.0 | 4.0 | 4.0 | 4.0 | 3.5 | 3.5 | 3.5 | 3.5 | 6.0 |
| Evaluation | Effect of restoring the flyaway and waved hair end to its original state | 19 | 19 | 18 | 18 | 18 | 18 | 20 | 14 | 16 | 9 | 9 |
| | Smoothness during application | 17 | 19 | 16 | 18 | 19 | 18 | 19 | 5 | 9 | 19 | 19 |
| | Smoothness during rinsing | 19 | 19 | 18 | 19 | 19 | 19 | 19 | 5 | 18 | 16 | 17 |

Example 8

Conditioner Composition (pH 3.2)

| | (wt. %) |
|---|---|
| Behenyltrimethylammonium chloride | 2.0 |
| Stearyl alcohol | 6.0 |
| p-Toluenesulfonic acid (70 wt. % aqueous solution) | 0.1 |
| Benzyloxyethanol | 0.7 |
| Dimethylpolysiloxane (polymerization degree: 600) | 1.0 |
| Highly polymerized dimethylpolysiloxane (polymerization degree 2600) | 1.2 |
| Decamethylcyclopentasiloxane | 1.5 |
| Amino-modified silicone-polyoxyalkylene block Copolymer ("FZ-3789", product of Dow Corning Toray Silicone) | 0.2 |
| Amino-modified silicone ("SM-8704C, product of Dow Corning Toray Silicone) | 0.2 |
| Lactic acid | 2.1 |
| Glycolic acid | 0.2 |
| Dipentaerythritol fatty acid ester ("Cosmol 168AR", product of Nisshin Oil Mills) | 0.2 |
| Hydroxyethyl cellulose ("SE-850K", product Of Daicel Chemical) | 0.3 |
| Hydrolyzed conchiolin (dry content: 3 wt. %) | 0.05 |
| Panax ginseng extract (dry content: 3 wt. %) | 0.05 |
| Soybean extract (dry content: 0.4 wt. %) | 0.05 |
| Eucalyptus extract (dry content: 0.2 wt. %) | 0.05 |
| Camellia oil | 0.05 |
| Rice bran oil | 0.05 |
| Perfume, methylparaben | q.s. |
| Purified water | Balance |

It has been found that the resulting hair conditioner was a hair cosmetic composition having a function of restoring the flyaway and waved hair, which had appeared as a result of accumulation of damage due to hair coloring or the like, to its former straight hair before damaged and capable of giving the hair good flexibility and smoothness during from wetting to drying and even after drying.

Example 9

Treatment Composition (pH 3.2)

| | (wt. %) |
|---|---|
| Stearamidopropyl dimethylamine ("Amidoamine MPS", product of Nikko Chemicals) | 2.0 |
| p-Toluenesulfonic acid | 0.1 |
| Stearyl alcohol | 6.5 |
| Behenyl alcohol | 1.5 |
| Isononyl isononanoate | 0.5 |
| Dimethylpolysiloxane (polymerization degree: 600) | 2.5 |
| Highly polymerized dimethylpolysiloxane (polymerization degree 2600) | 1.5 |
| Amino-modified silicone ("SM-8704C, product of Dow Corning Toray Silicone) | 1.0 |
| Lactic acid | 0.5 |
| Glycolic cid | 1.5 |
| Malic acid | 0.1 |
| Dipropylene glycol | 3.0 |
| Benzyl alcohol | 0.2 |
| Benzyloxyethanol | 1.5 |
| L-arginine (product of Kawaken Fine Chemicals) | 0.2 |
| Pantothenyl ethyl ether | 0.1 |
| Perfume, methylparaben | q.s. |
| Purified water | Balance |

It has been found that the resulting hair treatment composition was a hair cosmetic composition having a function of restoring the flyaway and waved hair, which had been appeared as a result of accumulation of damage due to hair coloring or the like, to its former straight hair before damage and capable of giving the hair good flexibility and smoothness during from wetting to drying and even after drying.

Example 10

Conditioner Composition (pH 3.2)

| | (wt. %) |
|---|---|
| Stearoxypropyltrimonium chloride | 2.0 |
| Behenyl alcohol | 8.0 |
| p-Toluenesulfonic acid | 0.1 |
| Sunflower oil | 2.0 |
| Benzyl alcohol | 1.0 |
| Dimethylpolysiloxane (polymerization degree: 2000) | 3.0 |
| Lactic acid | 0.5 |
| Hydrolyzed wheat protein | 0.2 |
| Carrot extract | 0.1 |
| Propylene glycol | 0.5 |
| Perfume | 0.3 |
| Purified water | Balance |

It has been found that the resulting hair conditioner was a hair cosmetic composition having a function of restoring the flyaway and waved hair, which had appeared as a result of accumulation of damage due to hair coloring, to the straight hair before damage and capable of giving the hair good flexibility and smoothness during from wetting to drying and even after drying.

The invention claimed is:

1. A hair cosmetic composition comprising the following components (A) to (C), and having a pH at 25° C. of from 1 to 5.5 when diluted to 20 times the weight of the composition with water:

(A) 0.5 to 5% of a cationic surfactant, or a tertiary amine represented by the formula (1):

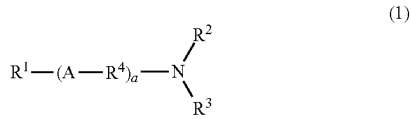

wherein, at least one of $R^1$ to $R^3$ represents an aliphatic hydrocarbon group having from 8 to 23 carbon atoms and the remainder represents a hydrogen atom, an alkyl or hydroxyalkyl group having from 1 to 6 carbon atoms or a benzyl group, $R^4$ represents an alkylene group having from 1 to 6 carbon atoms, A represents —CONH— or —NHCO— and a stands for 0 or 1; or salt thereof:

(B) 0.5 to 10% of an aliphatic alcohol having from 8 to 30 carbon atoms, and (C) 0.1 to 1% of toluenesulfonic acid or salt thereof, wherein the ratio of (A)/(C) ranges from 3 to 15.

2. The hair cosmetic composition according to claim 1, which comprises as Component (D) an organic solvent selected from the following (d1) to (d5):

(d1) compounds represented by the formula (4):

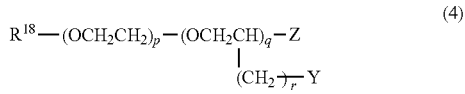

(4)

wherein, $R^{18}$ represents a hydrogen atom, an alkyl group having from 1 to 6 carbon atoms or a group $R^{19}$-Ph-$R^{20}$—, in which $R^{19}$ represents a hydrogen atom, a methyl group or a methoxy group, $R^{20}$ represents a bond or a saturated or unsaturated divalent hydrocarbon group having from 1 to 3 carbon atoms, and Ph represents a paraphenylene group, Y and Z each represents a hydrogen atom or a hydroxyl group, p, q and r each stands for an integer of from 0 to 5, with the proviso that when p=q=0, Z represents a hydroxyl group and $R^{18}$ represents neither a hydrogen atom nor a group $R^{19}$-Ph-, (d2) N-alkylpyrrolidones having a $C_{1-18}$ alkyl group bonded to a nitrogen atom, (d3) alkylene carbonates having from 2 to 4 carbon atoms, (d4) polypropylene glycols having a molecular weight of from 200 to 5000, and (d5) lactones or cyclic ketones represented by the following formula (5), (6) or (7):

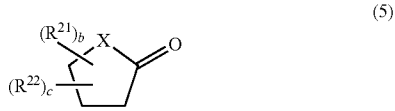

(5)

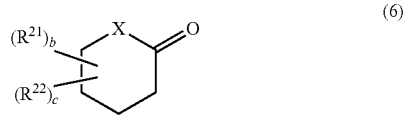

(6)

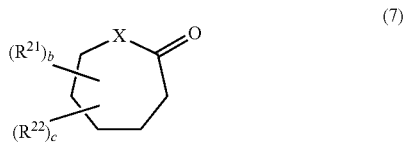

(7)

wherein, X represents a methylene group or an oxygen atom, $R^{21}$ and $R^{22}$ each independently represents a substituent selected from linear, branched or cyclic $C_{1-10}$ alkyl groups which may be substituted by a sulfonic acid group, phosphoric acid group or carboxyl group, a hydroxyl group, a sulfonic acid group, a phosphoric acid group, a carboxyl group and a phenyl group, and b and c each stands for 0 or 1.

3. The hair cosmetic composition according to claim 1, wherein component (A) is a cationic surfactant represented by the following formula (2):

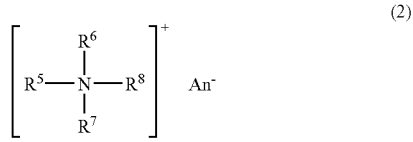

(2)

wherein, $R^5$ and $R^6$ each represents a hydrogen atom, an alkyl group having form 1 to 28 carbon atoms or a benzyl group, with the proviso that they do not simultaneously represent a hydrogen atom or a benzyl group and at least one of them represents an alkyl group having 8 or more carbon atoms, $R^7$ and $R^8$ each represents an alkyl or hydroxyalkyl group having from 1 to 5 carbon atoms or a polyoxyethylene group whose added molar number is 10 or greater in total, and $An^-$ represents an anion.

4. The hair cosmetic composition according to claim 1, wherein component (A) is at least one cationic surfactant selected from the group consisting of behenyltrimethylammonium chloride, stearyltrimethylammonium chloride, cetyltrimethylammonium chloride and arachyltrimethylammonium chloride.

5. The hair cosmetic composition according to claim 1, wherein component (A) is a cationic surfactant represented by the formula (3):

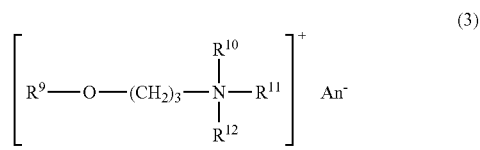

(3)

wherein, $R^9$ represents a linear or branched alkyl or alkenyl group having from 6 to 24 carbon atoms, $R^{10}$ to $R^{12}$ each represents an alkyl group having from 1 to 6 carbon atoms, benzyl group or —(BO)$_n$H (B representing an alkylene group having from 2 to 4 carbon atoms, n means an average number of moles added and it is from 1 to 6, and n pieces of B may be the same or different and may be arranged in any order), and $An^-$ represents an anion.

6. The hair cosmetic composition according to claim 1, wherein component (A) is a tertiary amine of formula (1) and a=0.

7. The hair cosmetic composition according to claim 1, wherein component (A) is a tertiary amine of formula (1), A represents —CONH— and a stands for 1.

8. The hair cosmetic composition according to claim 1, wherein component (A) is at least one tertiary amine selected from the group consisting of dimethyldecylamine, dimethyllaurylamine, dimethylmyristylamine, dimethylpalmitylamine, dimethylstearylamine, dimethyloctylamine, dimethylbehenylamine, dilaurylmonomethylamine and trioctylamine.

9. The hair cosmetic composition according to claim 1, wherein component (A) is a tertiary amine of formula (1) represented by the formula (1b)

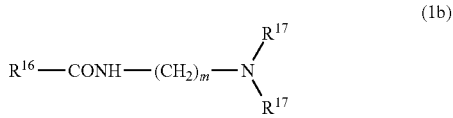

(1b)

wherein, $R^{16}$ represents an aliphatic hydrocarbon group having from 11 to 23 carbon atoms, $R^{17}$s may be the same or different and each represents a hydrogen atom or an alkyl group having from 1 to 4 carbon atoms, and m stands for an integer of from 2 to 4.

10. The hair cosmetic composition according to claim 1, wherein component (A) is at least one tertiary amine selected from the group consisting of stearic acid dimethylaminoethylamide, stearic acid dimethylaminopropylamide, stearic acid diethylaminoethylamide, stearic acid diethylaminopropylamide, stearic acid dipropylaminoethylamide, stearic acid dipropylaminopropylamide, palmitic acid dimethylaminoethylamide, palmitic acid dimethylaminopropylamide, myristic acid dimethylaminoethylamide, myristic acid dimethylaminopropylamide, behenic acid dimethylaminoethylamide and behenic acid dimethylaminopropylamide.

11. The hair cosmetic composition according to claim 1, wherein component (A) is a tertiary amine which is neutralized with an acid.

12. The hair cosmetic composition according to claim 11, wherein said acid is an organic acid which is use in an amount of from 0.1 to 10 times the moles of the tertiary amine.

13. The hair cosmetic composition according to claim 1, wherein said aliphatic alcohol is at least one selected from the group consisting of cetyl alcohol, stearyl alcohol, aralkyl alcohol and behenyl alcohol, of which stearyl alcohol and behenyl alcohol.

14. The hair cosmetic composition according to claim 1, wherein a molar ratio of Component (A) to Component (B) is from 0.8/2 to 0.8/15.

15. The hair cosmetic composition according to claim 2, wherein a content of said organic solvent in the hair cosmetic composition is from 0.01 to 20 wt. %.

16. The hair cosmetic composition according to claim 1, further comprising a silicone compound.

17. The hair cosmetic composition according to claim 15, wherein said silicone compound is incorporated in an amount of from 1 to 15 wt. %.

18. A method of restoring flyaway or waved hair, which has been caused by the accumulation of damage due to hair coloring, to its former straight hair comprising applying an effective amount of the hair cosmetic composition according to claim 1 to the hair of a subject in need thereof, rinsing said hair, and drying said hair.

* * * * *